(12) United States Patent
Wiesmann et al.

(10) Patent No.: US 7,080,646 B2
(45) Date of Patent: Jul. 25, 2006

(54) SELF-CONTAINED MICROMECHANICAL VENTILATOR

(75) Inventors: William P. Wiesmann, Washington, DC (US); Protagoras N. Cutchis, Highland, MD (US); Loland Alex Pranger, Montgomery Village, MD (US)

(73) Assignee: Sekos, Inc., Germantown, MD (US)

( * ) Notice: Subject to any disclaimer, the term of this patent is extended or adjusted under 35 U.S.C. 154(b) by 557 days.

(21) Appl. No.: 10/228,166

(22) Filed: Aug. 26, 2002

(65) Prior Publication Data

US 2004/0035424 A1     Feb. 26, 2004

(51) Int. Cl.
*A61M 16/00*     (2006.01)
(52) U.S. Cl. ............................. 128/204.26; 128/204.18
(58) Field of Classification Search ..............................
128/200.14–200.24, 203.12, 203.23, 204.18,
128/204.21–204.23, 205.24, 207.14–207.18
See application file for complete search history.

(56) References Cited

U.S. PATENT DOCUMENTS

| | | | | |
|---|---|---|---|---|
| 4,080,103 A | * | 3/1978 | Bird ............................. | 417/3 |
| 4,592,349 A | * | 6/1986 | Bird ....................... | 128/204.25 |
| 4,681,099 A | * | 7/1987 | Sato et al. ............. | 128/204.23 |
| 5,868,133 A | * | 2/1999 | DeVries et al. ........ | 128/204.21 |
| 2003/0172931 A1 | | 9/2003 | Derechanin, II et al. | |

* cited by examiner

*Primary Examiner*—Glenn K. Dawson
(74) *Attorney, Agent, or Firm*—Abanti Bhattacharyya, Esq.; Bartunek & Bhattacharyya, Ltd.

(57) ABSTRACT

The portable ventilators of the present invention provide a hands-free ventilatory support device in critical care, emergency and resource limited environments. The portable ventilators utilize ambient air and include a two dual head compressor system to provide a consistent air supply to the patient. The ventilator device is battery operated and is capable of providing up to 60 minutes of care.

16 Claims, 5 Drawing Sheets

SELF-CONTAINED MICROMECHANICAL VENTILATOR

BACKGROUND OF THE INVENTION

Immediate medical care can save the lives of countless accident victims and military personnel. In the emergency medical services arena, there has long been an emphasis on the golden hour during which a patient must receive definitive medical attention. However, definitive medical attention is often limited, because of the lack of necessary equipment. While state of the art medical equipment can be found in medical facilities, such is not the case in emergency situations or military applications. This is particularly true in the area of ventilators.

Inspiration-only ventilators are known and widely used in hospital settings as they provide useful breathing circuits while minimizing the amount of oxygen utilized in treating the patient.

Current ventilators are generally designed for stationary, medical facilities. They are heavy, cumbersome and ill suited for portable applications. Most ventilators utilize medical grade air or highly flammable, compressed canisters of oxygen for its oxygen sources. These tanks air/oxygen are heavy, cumbersome, and unsuitable for transport. Prior-art ventilators also require large power sources, making them even less suitable for quick, on-site use. Lastly, most known ventilators require operation by trained personnel in treatment environments, where additional equipment and resources are easily available.

For example, U.S. Pat. No. 5,664,563 to Schroeder et al disclose a computer controlled pneumatic ventilator system that includes a double venturi drive and a disposable breathing circuit. The double venturi drive provides quicker completion of the exhalation phase leading to an overall improved breathing circuit. The disposable breathing circuit allows the ventilator to be utilized by multiple patients without risk of contamination. This device utilizes canistered oxygen sources. This device also would be rendered inoperable under the conditions anticipated by the present invention.

Therefore, there is a need for portable ventilators that overcome the disadvantages of the existing stationary ventilators.

The following portable ventilators address some of the needs discussed above. U.S. Pat. Nos. 6,152,135, 5,881,722 and 5,868,133 to DeVries et al. discloses a portable ventilator device that utilizes ambient air through a filter and a compressor system. The compressor operates continuously to provide air only during inspiration. The DeVries et al devices are utilized in hospital settings and are intended to provide a patient with mobility when using the ventilator. Since these devices are not directed to on-site emergency use, they provide closed loop control, sophisticated valving systems and circuitry that would render them inoperable under the types of emergency conditions anticipated by the present invention.

The references cited above recognize the need for portable ventilators that provide a consistent breathing circuit. As is the case with most portable ventilators, these devices provide breathing circuits including valve systems and an oxygen source. However, these devices lack the means by which they can be quickly facilitated in emergency situations where there are no stationary sources of power. Secondly, most of these devices depend on canister-style oxygen sources, which are cumbersome, and lessen the ability of the ventilators to be truly portable. Thirdly, the prior art ventilators do not provide breathing circuits that can be continuously used in the absence of stationary power sources. These and other drawbacks are overcome by the present invention as will be discussed, below.

SUMMARY OF THE INVENTION

It is therefore an objective of this invention to provide a portable ventilator that provides short-term ventilatory support.

It is another objective of the present invention to provide a portable ventilator that includes a pneumatic subsystem, a power subsystem and a sensor subsystem.

It is another objective of the present invention to provide a portable ventilator wherein the pneumatic subsystem includes two dual head compressor for increased air output.

It is another objective of the present invention to provide a portable ventilator wherein the pneumatic subsystem includes an accumulator.

It is another objective of the present invention to provide a portable ventilator that is a disposable one-use device having an indefinite shelf life.

These and other objectives have been described in the detailed description provided below.

DETAILED DESCRIPTION OF THE EMBODIMENTS

Figure 1:
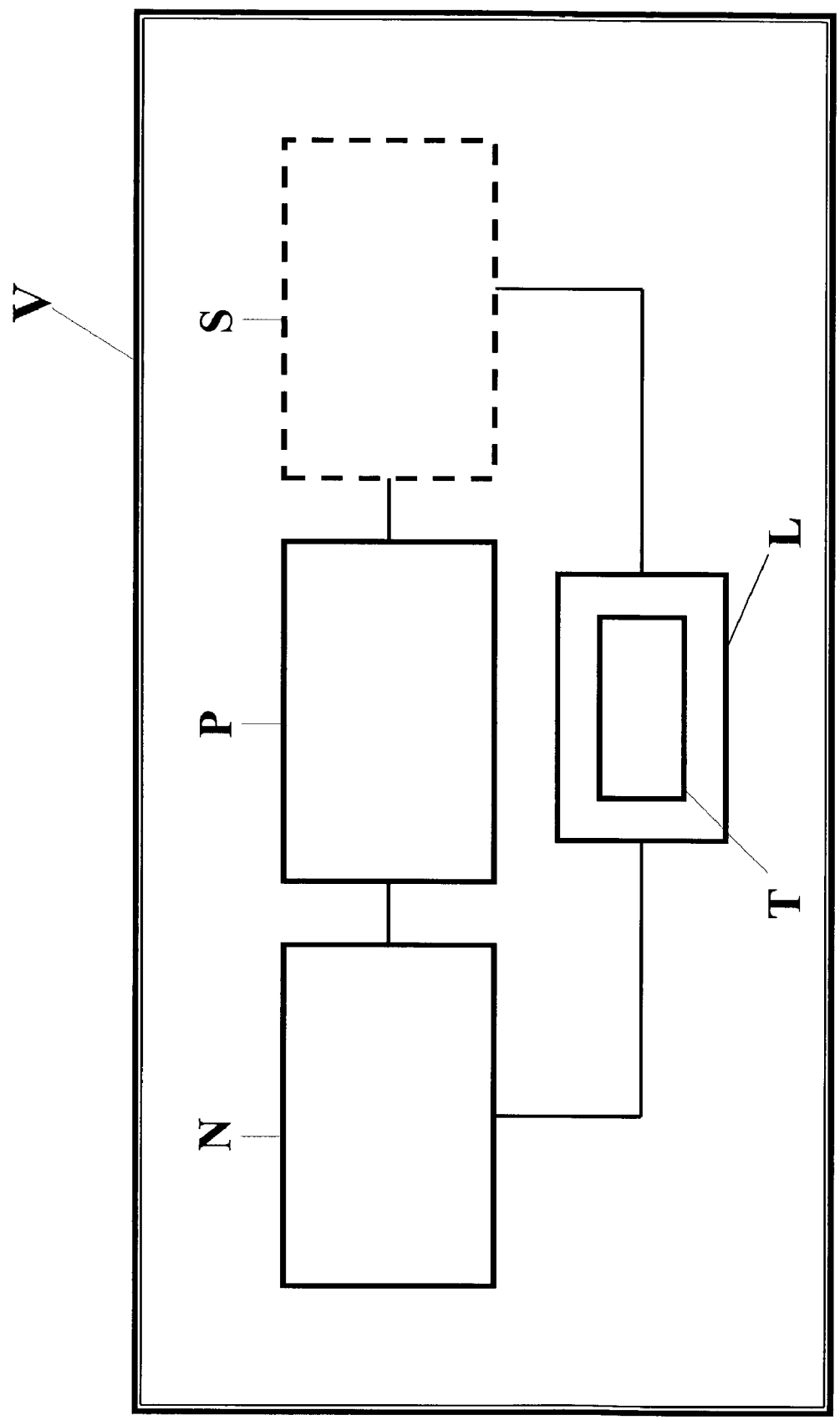
FIG. 1 is a schematic of the portable ventilator, the pneumatic subsystem, the power subsystem and the sensor subsystem.

The present invention is a portable ventilator that provides short-term ventilatory support to one or more patients for the management of trauma or respiratory paralysis. As shown in FIG. 1, the portable ventilator V assures consistent tidal volume and respiratory rate and provides hands free operational capabilities. The portable ventilator V is a fully functional multi-mode device suited for field hospital or forward surgical units, where experienced personnel can utilize the multi-mode capabilities unique to this device. Portable ventilator V is also suitable for use by untrained personnel, and in particularly useful in resource-limited environments. Additionally, the portable ventilator V can be configured as a disposable one-use device that has an indefinite shelf life.

Also in FIG. 1, the portable ventilator V of the present invention includes a pneumatic subsystem N, a power subsystem P, and a sensor subsystem S. Each of these systems shall be described below.

Figure 2:
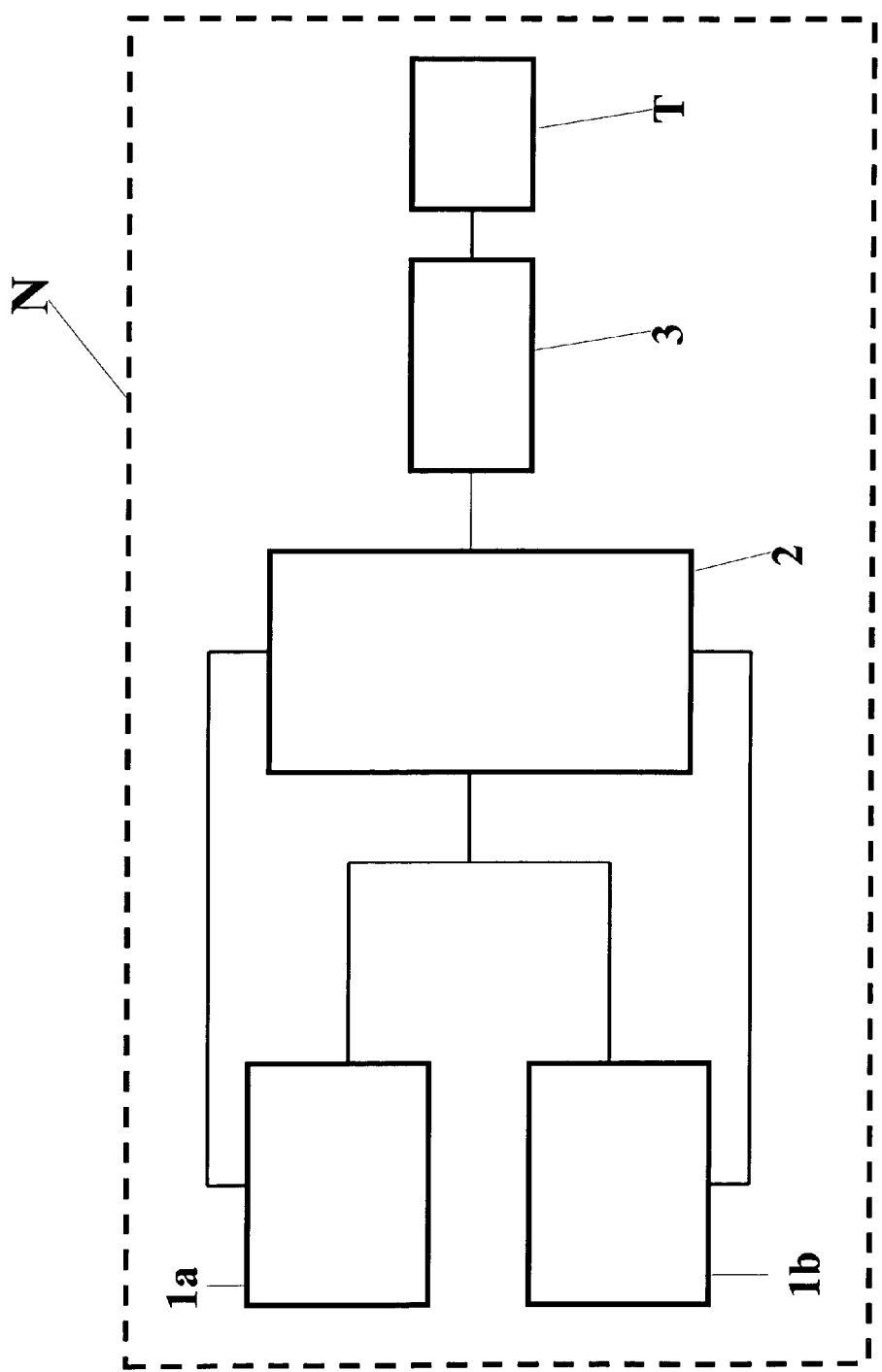
FIG. 2 is a schematic of the pneumatic subsystem.

The Pneumatic Subsystem:

As shown in FIG. 2, the pneumatic subsystem N includes two dual head air compressors 1a and 1b for increased air output. Ambient or NVC filtered air is drawn into the dual head compressors 1a and 1b and compressed. The compressed air exits 1a and 1b and enters into the accumulator tank 2. An accumulator tank 2 is connected to each of the compressors 1a and 1b to act as a pneumatic holding area for the combined outputs (4 in total) of compressors 1a and 1b. The accumulator tank 2 overcomes the inconsistent nature of the phasing of the pressure waves inherent with dual head air compressors and prevents compressors 1a and 1b outputs from canceling each other. The accumulator tank 2 is further connected to a connector system 3. Since the compressors 1a and 1b function as constant-flow rates over a wide range of physiologic pressures, the connector system 3 provides constant, total airflow through the accumulator 2 to the user, for a necessary period of time. The periods of time are controlled through a timing circuit T that is part of a logic board B.

The Logic Board:

The logic board B includes timing circuit T and is connected to the power subsystem P. Logic board B controls power to compressors 1a and 1b in order to turn 1a and 1b on and off. Duration of the on-time of compressors 1a and 1b determines the amount of air that is delivered to the user. The logic board B utilizes analog logic and does not require microprocessor control. The logic board B is also connected to the sensor subsystem S.

Figure 3:
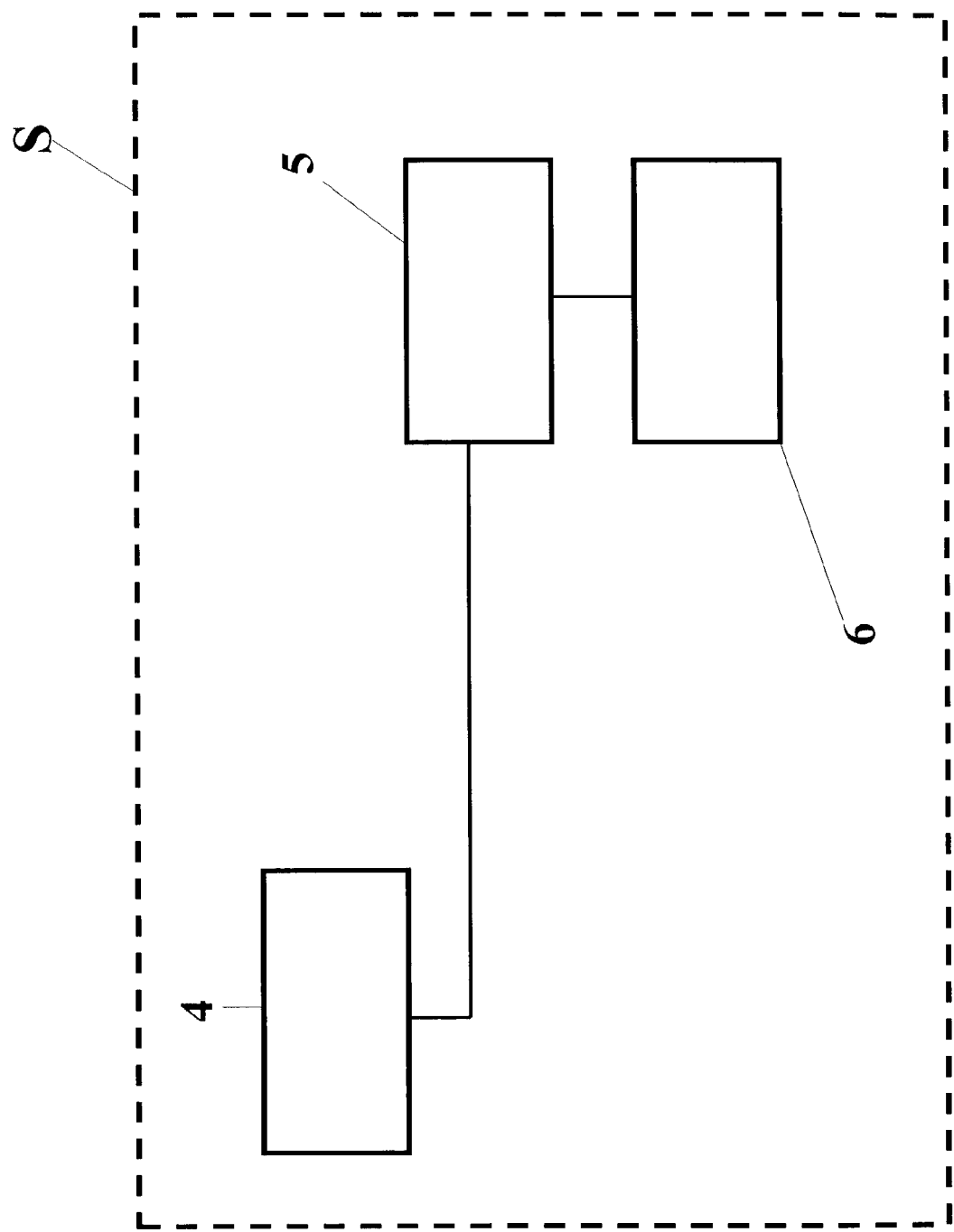
FIG. 3 is a schematic of the power subsystem.

The Sensor Subsystem:

As shown in FIG. 3, the portable ventilator V includes a sensor subsystem S that provides critical care monitoring and support critically ill patients in the emergency situations. The sensor subsystem S includes an airflow sensor 4 that detects loss of connection of the portable ventilator V from the patient's face mask or endotracheal tube. The sensor subsystem S also includes an airway pressure sensor 5. The pressure sensor 5 provides the desirable function of detecting the end of a previous breath (inhaled) in the user, so that air delivery can be delayed until the completion of the previous breath. An airflow sensor 6 is used to detect the cessation of exhalation of the previous breath if the scheduled start time for the next breath is not completed. The sensor subsystem S may be located within the ventilator V or be exterior to ventilator V.

Figure 4:
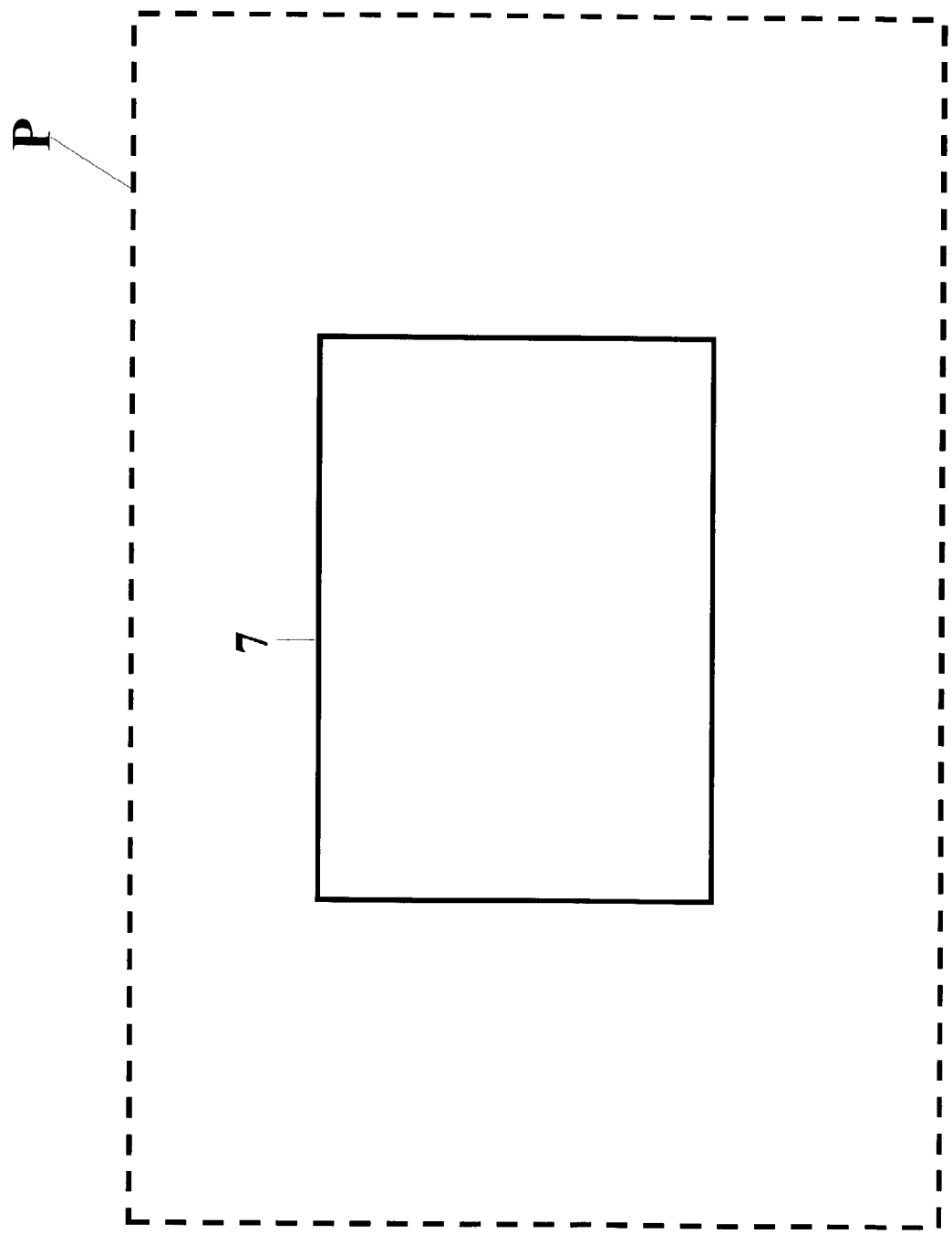
FIG. 4 is a schematic of the sensor subsystem.

The Power Subsystem:

As shown in FIG. 4, the power subsystem P of the portable ventilator V include disposable or rechargeable batteries 7 that are capable of operating under high capacity, wide temperature ranges and are compatible with the pneumatic subsystem N and the sensor subsystem S. In a preferred embodiment, the portable ventilator V of the present invention utilizes conventional lead-acid rechargeable batteries 7. The batteries 7 must provide at least 30 to 60 minutes of operating time.

Figure 5:
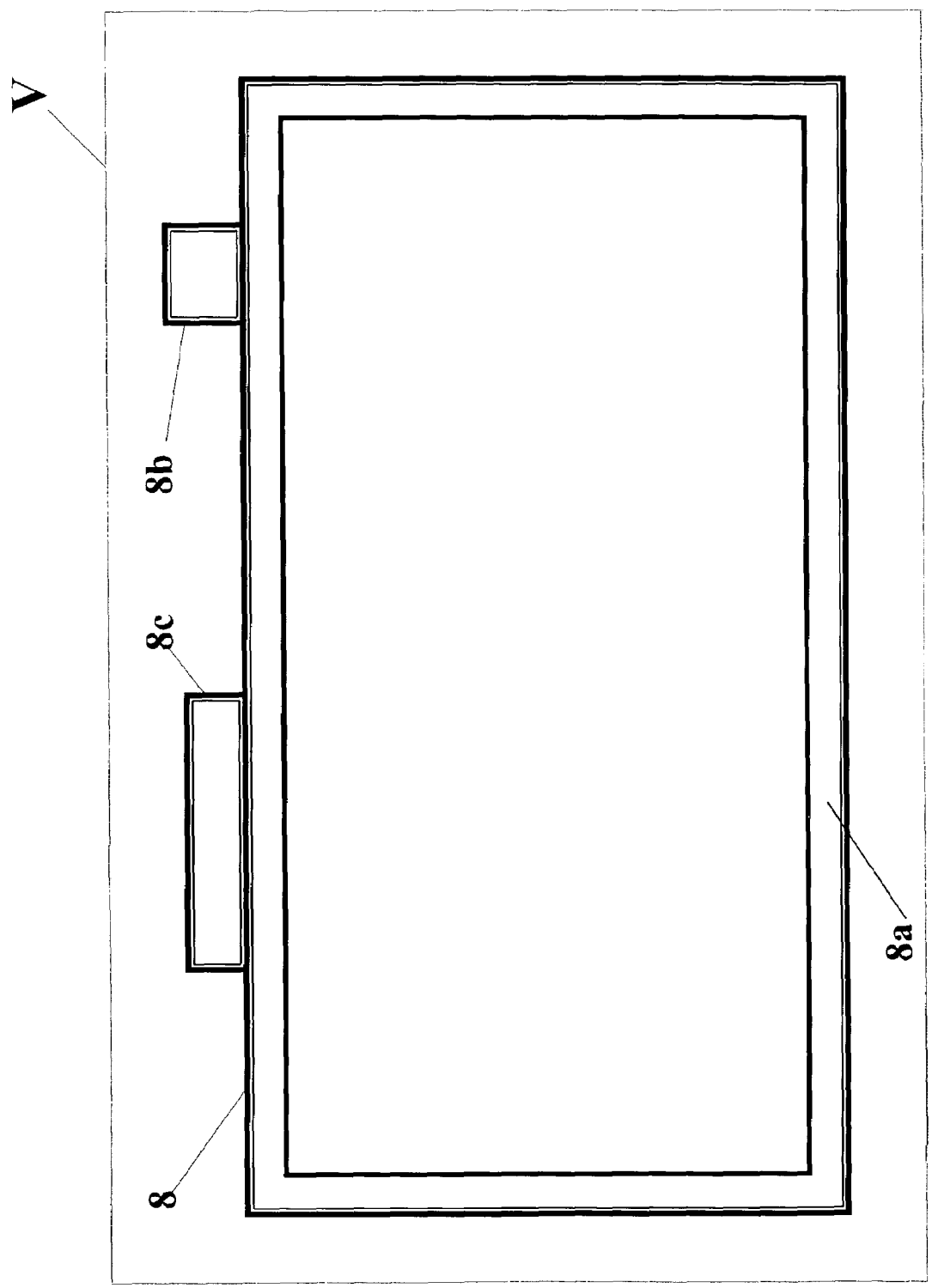
FIG. 5 is a drawing of the portable ventilator.

The Portable Ventilator:

As shown in FIG. 5, the pneumatic subsystem N is connected to the sensor subsystem S and the power subsystem P and enclosed within housing 8 of the portable ventilator V. Housing 8 includes an rigid frame structure 8a that is made of either plastic or metals and capable of withstanding physical and mechanical pressures. Portable ventilator V includes an input port 8b which allows rechargeable batteries 7 to be powered using an external power source or an AC power source. Alternatively, batteries 7 may include disposable type batteries.

Housing 8 also a recessed control panel 8c. Control panel 8c includes ports for providing air to the user through known means. The panel 8c also includes a switch for selecting desired air flow rates, an on/off switch and can include a switch for recharging the batteries 7. The control panel 8c is recessed to prevent damage to any instrumentation positioned thereon.

The portable ventilator V of the present invention implements controlled ventilation and assists control ventilation to a patient. Example 1 below shows functionality and performance of two portable ventilators V described above.

EXAMPLE1

The Sekos 2 and 3 ventilators were tested. All tidal volumes, respiratory rates and other parameters were within Ÿ10% of the settings existing on the ventilator V.

| PERFORMANCE PARAMETER | SEKOS 2 | SEKOS 3 |
|---|---|---|
| APPROX. WEIGHT (lb0 | 12 | <6 |
| APPROX. SIZE (in.) | 10.75W × 9 75D × 7 H | 5.7W × 11 5D × 3 5H |
| PHYSICAL VOLUME (in³) | 733 | 230 |
| BATTERY TYPE/SIZE | 3.4 Ah lead acid | 1.3 Ah lead acid |
| OPERATING LIFE (h) | 1.5–3 | 0.3–1 |
| COMPRESSORS | 2 | 2 |
| CONTROLLABLE I:E RATIO | No | No |
| RESP. RATE ADJUSTMENT (bpm) | 6–30 | 10 OR 20 ONLY |
| TIDAL VOLUME (ml) | 200–1200 | 300, 900, OR 1200 |
| MAX MINUTE VOLUME (L/m) | 20 (NOT YET TESTED) | 20 (NOT YET TESTED) |
| INSPIRATORY FLOW MEASUREMENT | No | No |
| EXPIRATORY FLOW MEASUREMENT | Yes | Yes |

The portable ventilators tested above, have been shown to be superior in performance to traditional ▓ambu-bags▓. These and other portable ventilators having the features discussed above are within the scope of this invention.

The invention claimed is:

1. A portable ventilator system comprising a pneumatic subsystem, a power subsystem, a sensor subsystem and a logic board;

said logic board further comprising a timing circuit and connected to each of said subsystems;

said pneumatic subsystem, said power subsystem and said logic board further constructed so as to be enclosed within a housing having a recessed control panel;

said pneumatic subsystem further comprising first and second dual head air compressors, said first and second compressor each further comprising two outputs, said compressors constructed so as to compress ambient air;

an accumulator tank connected to each of said two outputs of said first compressor and said two outputs of said second compressor, so as to hold combined outputs of compressed air from each of said compressors;

a connector system, said connector system constructed so as to provide constant, total airflow through said accumulator to a user over a period of time, wherein said logic board is constructed so as to not require microprocessor control; and wherein said logic board is further constructed so as to control said air that is delivered to said user.

2. A portable ventilator system as recited in claim 1 wherein said sensor subsystem comprises an airflow sensor, said sensor constructed so as to detect loss of connection of said portable system from said user.

3. A portable ventilator system as recited in claim 2, wherein said sensor subsystem further comprises an airway pressure sensor, said sensor constructed so as to detect end of a previous breath in said user.

4. A portable ventilator system as recited in claim 3 wherein said sensor subsystem further comprises an airflow sensor, said sensor constructed so as to detect cessation of exhalation of said previous breath.

5. A portable ventilator system as recited in claim 4, wherein said power subsystem comprises batteries constructed so as to operate under high capacity, in wide temperature ranges;

said batteries further constructed so as to operate for at least 30 to 60 minutes; and said batteries further constructed so as to be compatible with said pneumatic subsystem and said sensor subsystem.

6. A portable ventilator system as recited in claim 5, wherein said batteries are selected from the group consisting of rechargeable batteries and disposable batteries.

7. A portable ventilator system as recited in claim 6, wherein said housing comprises a rigid frame structure, wherein said structure is constructed so as to withstand physical and mechanical pressures.

8. A portable ventilator system as recited in claim 7 wherein said housing comprises an input port, said port constructed so as to allow said rechargeable batteries to be powered by an external power source.

9. A portable ventilator system as recited in claim 8, wherein said recessed control panel further comprises a first switching means for selecting desired flow rates.

10. A portable ventilator system as recited in claim 9, wherein said recessed control panel further comprises a second switching means for recharging said batteries.

11. A method for providing a person with ventilatory care comprising:

using a portable ventilator having first and second dual head compressors and an accumulator tank, wherein each of said first and second compressors further comprise two outputs to said accumulator;

housing a power subsystem in said portable ventilator and connecting said compressors and said accumulator tank to said power subsystem; and connecting a sensor subsystem to said power subsystem, said compressors and said accumulator tank.

12. A method for providing a person with ventilatory care as recited in claim 11 and further comprising the steps of:

(a) drawing air into said first and second dual head compressors and increasing amount of said air being drawn into said first and second compressors;

(b) compressing said air in said first and second compressors and maintaining constant flow rates of said air over a wide range of physiologic pressures;

(c) moving said air from two outputs of said first dual head compressor and two outputs of said second dual head compressor into said accumulator tank, and holding a combined quantity of said compressed air from said first and second compressor in said accumulator tank;

(d) supplying said person with constant flow rates of said air over a necessary period of time.

13. A method for providing a person with ventilatory care as recited in claim 12, and further comprising controlling said necessary periods of time using a non-microprocessor driven logic board having a timing circuit.

14. A method for providing a person with ventilatory care as recited in claim 13, and further comprising determining duration of on-time of said first and second compressors and further determining an amount of air being delivered to said person.

15. A method for providing a person with ventilatory care as recited in claim 14 and further comprising detecting loss of connection of said portable ventilator from said person using an air flow sensor of said sensor subsystem.

16. A method for providing a person with ventilatory care as recited in claim 15 and further comprising using a pressure sensor of said sensor subsystem and detecting end of a previous inhaled breath in said person and delaying delivery of said air to said person until completion of said previous breath.

* * * * *